US010165942B2

United States Patent
Uji et al.

(10) Patent No.: US 10,165,942 B2
(45) Date of Patent: Jan. 1, 2019

(54) OPTICAL TOMOGRAPHIC IMAGING APPARATUS, CONTROL METHOD THEREFOR, AND PROGRAM THEREFOR

(71) Applicant: CANON KABUSHIKI KAISHA, Tokyo (JP)

(72) Inventors: Akihito Uji, Kyoto (JP); Nagahisa Yoshimura, Kyoto (JP); Hirofumi Yoshida, Yokohama (JP); Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/534,559

(22) PCT Filed: Jan. 7, 2016

(86) PCT No.: PCT/JP2016/000045
§ 371 (c)(1),
(2) Date: Jun. 9, 2017

(87) PCT Pub. No.: WO2016/111248
PCT Pub. Date: Jul. 14, 2016

(65) Prior Publication Data
US 2017/0332898 A1    Nov. 23, 2017

(30) Foreign Application Priority Data

Jan. 9, 2015    (JP) ................................ 2015-003427

(51) Int. Cl.
*A61B 3/14*        (2006.01)
*A61B 3/10*        (2006.01)
(Continued)

(52) U.S. Cl.
CPC ............ *A61B 3/102* (2013.01); *A61B 3/0041* (2013.01); *A61B 3/12* (2013.01); *A61B 3/14* (2013.01)

(58) Field of Classification Search
CPC ......... A61B 3/102; A61B 5/0066; A61B 3/14; A61B 3/12; A61B 5/0073; A61B 3/0025;
(Continued)

(56) References Cited

U.S. PATENT DOCUMENTS

| 7,980,696 B1 | 7/2011 | Taki et al. |
| 8,294,901 B2 | 10/2012 | Yoshida et al. |

(Continued)

FOREIGN PATENT DOCUMENTS

| EP | 2 347 701 A1 | 7/2011 |
| EP | 2 853 192 A1 | 4/2015 |

(Continued)

OTHER PUBLICATIONS

Mar. 24, 2016 International Search Report and Written Opinion in International Patent Appln. No. PCT/JP2016/000045.
(Continued)

*Primary Examiner* — Brandi Thomas
(74) *Attorney, Agent, or Firm* — Venable LLP

(57) ABSTRACT

Focus adjustment is enabled with respect to an object to be inspected even when an optical member for changing a field angle is inserted in order to change the field angle of an acquiring area of a tomographic image, and a clear tomographic image with a focus on the object to be inspected is acquired. In an optical tomographic imaging apparatus, an optical system includes a focus lens configured to focus a measuring light on the object to be inspected. The optical tomographic imaging apparatus includes a unit configured to compensate, when an optical member for changing a field angle is inserted between a scanning unit and the object to be inspected in order to change the field angle of an acquiring area of a tomographic image, a change in a focus position of the focus lens in association with the inserting.

14 Claims, 4 Drawing Sheets

(51) Int. Cl.
*A61B 3/00* (2006.01)
*A61B 3/12* (2006.01)

(58) Field of Classification Search
CPC ... A61B 3/1005; A61B 3/1025; A61B 3/0041; A61B 3/1225; A61B 5/6852; A61B 3/10; A61B 3/107; A61B 3/1233; A61B 5/0084; A61B 3/0091; A61B 5/7203; A61B 1/00009; A61B 1/001
USPC ........ 351/200, 205, 206, 209–211, 221, 222, 351/243–246
See application file for complete search history.

(56) References Cited

U.S. PATENT DOCUMENTS

| | | | |
|---|---|---|---|
| 8,308,297 B2 | 11/2012 | Hirose et al. |
| 8,425,036 B2 | 4/2013 | Yoshida et al. |
| 8,919,959 B2 | 12/2014 | Makihira |
| 8,950,863 B2 | 2/2015 | Makihira |
| 8,960,904 B2 | 2/2015 | Aoki et al. |
| 8,960,905 B2 | 2/2015 | Aoki et al. |
| 8,992,018 B2 | 3/2015 | Makihira |
| 8,998,412 B2 | 4/2015 | Makihira |
| 9,004,685 B2 | 4/2015 | Iwase et al. |
| 9,055,891 B2 | 6/2015 | Suehira et al. |
| 9,109,870 B2 | 8/2015 | Bajraszewski et al. |
| 9,113,820 B2 | 8/2015 | Utagawa et al. |
| 9,161,690 B2 | 10/2015 | Tomatsu et al. |
| 9,237,845 B2 | 1/2016 | Numajiri et al. |
| 9,291,445 B2 | 3/2016 | Yoshida |
| 9,310,187 B2 | 4/2016 | Bajraszewski et al. |
| 9,330,299 B2 | 5/2016 | Makihira |
| 9,351,650 B2 | 5/2016 | Uji et al. |
| 9,386,920 B2 | 7/2016 | Akita |
| 9,408,532 B2 | 8/2016 | Makihira |
| 9,468,374 B2 | 10/2016 | Makihira |
| 9,545,199 B2 | 1/2017 | Wang et al. |
| 9,687,148 B2 | 6/2017 | Makihira |
| 2012/0002166 A1 | 1/2012 | Tomatsu et al. |
| 2012/0154747 A1 | 6/2012 | Makihira |
| 2012/0250029 A1 | 10/2012 | Yoshida |
| 2013/0021575 A1 | 1/2013 | Yoshida et al. |
| 2013/0215387 A1 | 8/2013 | Makihira et al. |
| 2014/0128821 A1 | 5/2014 | Gooding et al. |
| 2014/0211156 A1* | 7/2014 | Masaki | A61B 3/0033 351/206 |
| 2014/0211159 A1 | 7/2014 | Komine et al. |
| 2014/0240667 A1 | 8/2014 | Uji et al. |
| 2014/0253926 A1 | 9/2014 | Lee et al. |
| 2014/0313478 A1* | 10/2014 | Shikaumi | A61B 3/14 351/206 |
| 2014/0313479 A1 | 10/2014 | Nozato et al. |
| 2015/0305617 A1 | 10/2015 | Tachikawa et al. |
| 2016/0157713 A1 | 6/2016 | Yoshida |

FOREIGN PATENT DOCUMENTS

| | | | | |
|---|---|---|---|---|
| JP | 2 347 701 | * | 7/2011 | ............. A16B 3/117 |
| JP | 2011-147609 A | | 8/2011 | |
| JP | 2011-147612 A | | 8/2011 | |
| KR | 10-2014-0107831 A | | 9/2014 | |
| WO | 2015/044121 A1 | | 4/2014 | |

OTHER PUBLICATIONS

Jul. 20, 2017 International Preliminary Report on Patentability in International Patent Appln. No. PCT/JP2016/000045.

* cited by examiner

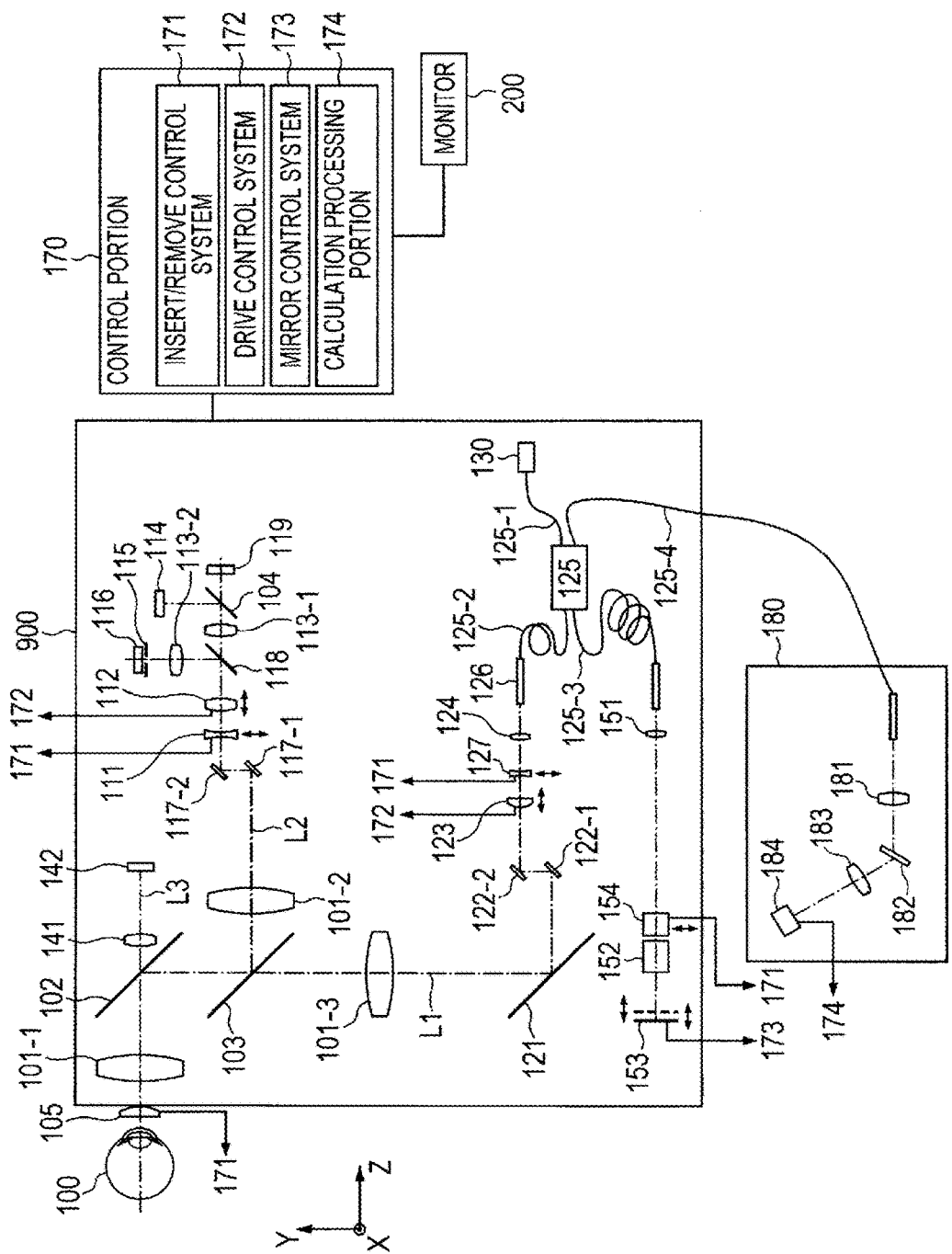
[Fig. 1]

[Fig. 2]
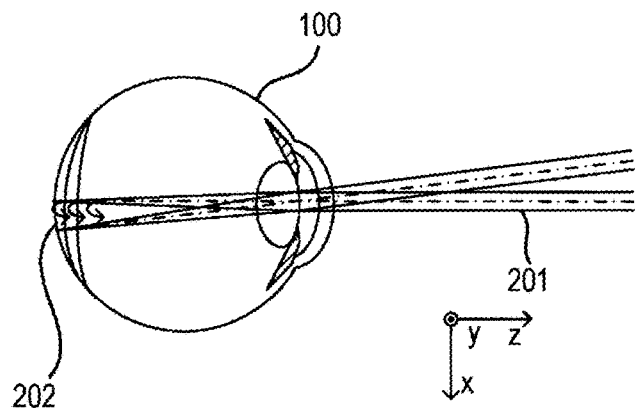
[Fig. 3]
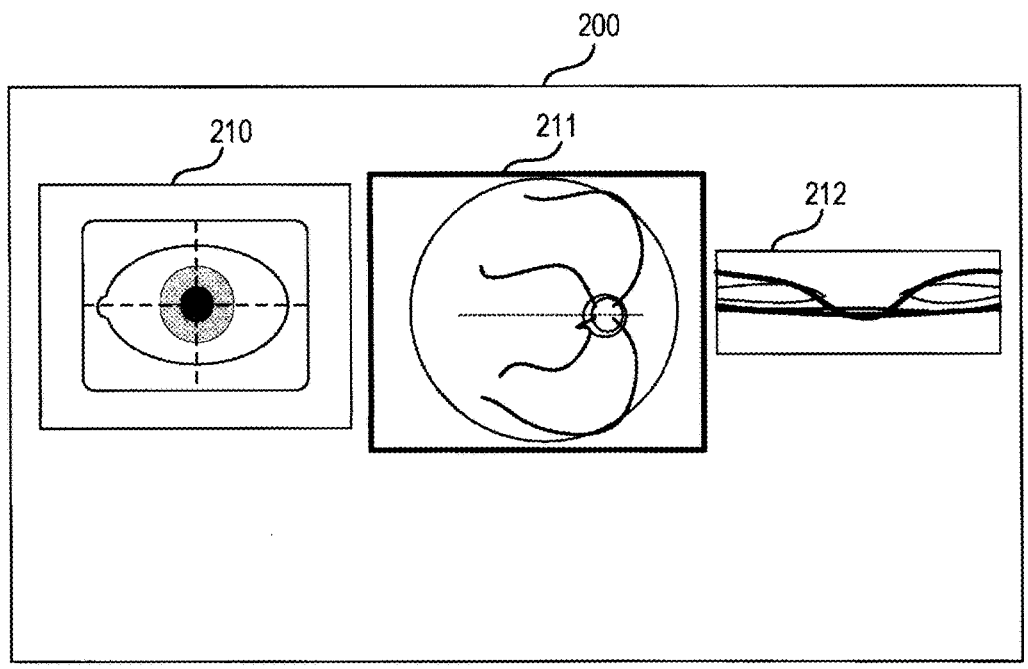

[Fig. 4]
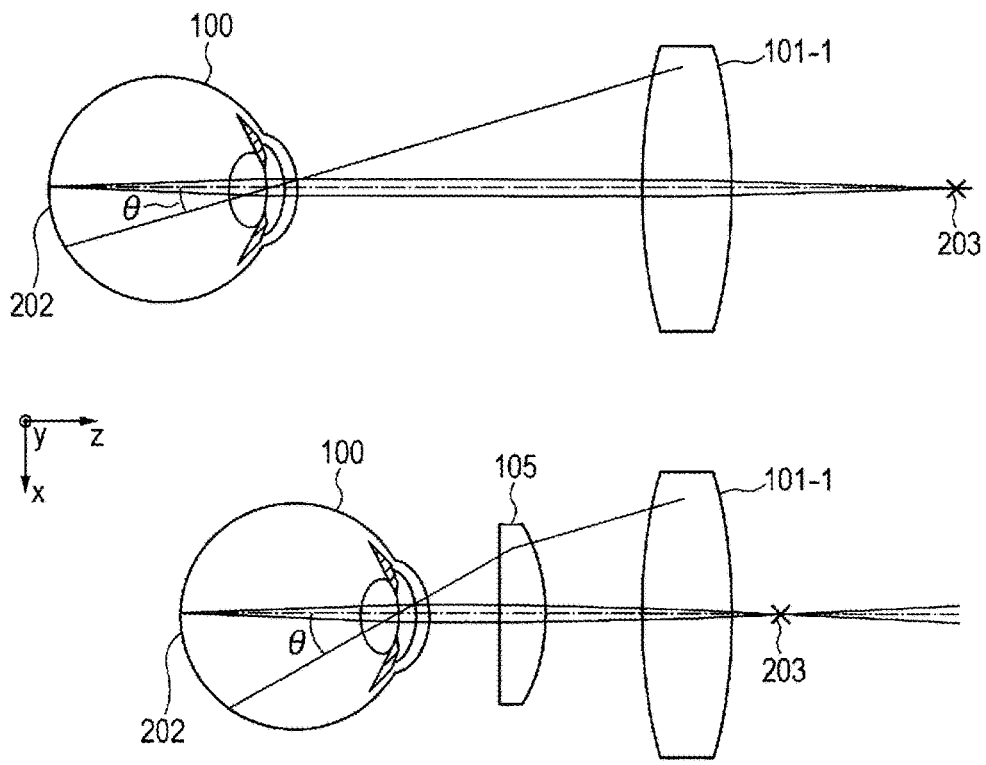
[Fig. 5]
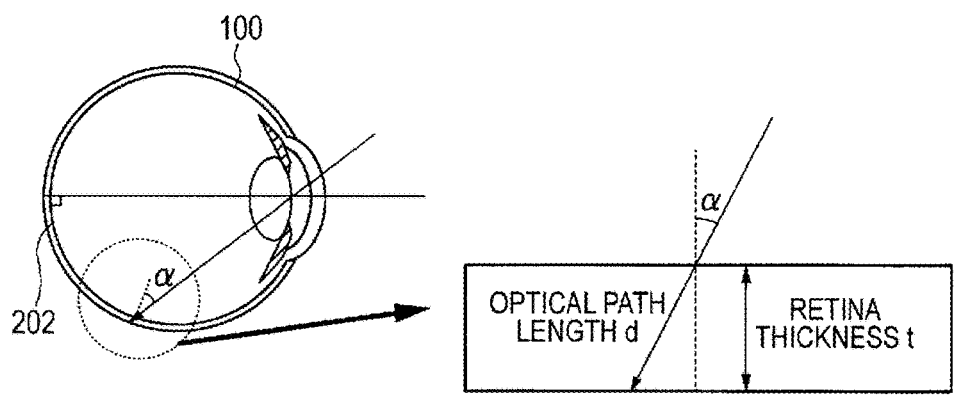

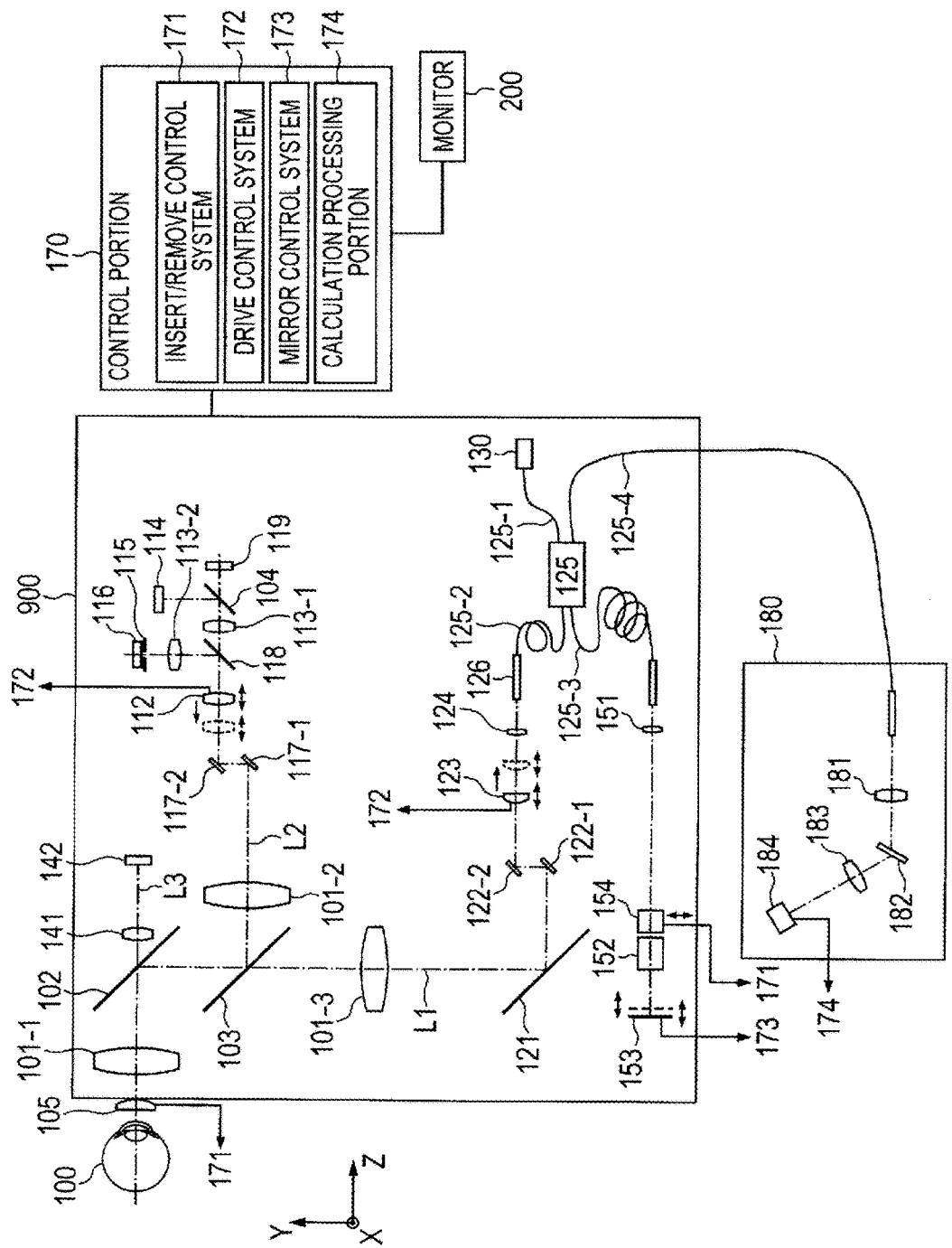
[Fig. 6]

OPTICAL TOMOGRAPHIC IMAGING APPARATUS, CONTROL METHOD THEREFOR, AND PROGRAM THEREFOR

TECHNICAL FIELD

The present invention relates to an optical tomographic imaging apparatus configured to image a tomographic image of an object to be inspected, a control method therefor, and a program for executing the control method.

BACKGROUND ART

There is developed an optical tomographic imaging apparatus (hereinafter referred to as "OCT apparatus") configured to image a tomographic image of an object to be inspected through use of optical coherence tomography (hereinafter referred to as "OCT"). In the OCT apparatus, an object is irradiated with a measuring light being a low-coherence light, and a scattered light or a reflected light from the object is caused to interfere with a reference light, to thereby obtain an interference light. Then, a frequency component of a spectrum of the interference light is analyzed, to thereby obtain the tomographic image of the object with high resolution. Such an OCT apparatus is suitably used for a fundus inspection for conducting a medical inspection of an eye to be inspected by obtaining a tomographic image of a fundus of the eye to be inspected.

In regard to an ocular disease, it is important to discover a lesion of the fundus at an early stage, and to start treatment to delay the progress of the lesion extending over a wide area of the fundus at an early stage. In particular, a profound effect is exerted on a visual sense when the lesion reaches a macula, which raises a demand that the lesion be discovered even when the lesion exists at a position sufficiently distant from the macula. In order to meet the demand, the OCT apparatus used for the fundus inspection is expected to have a wider field angle.

In Patent Literature 1 (PTL 1), there is disclosed a configuration in which an adapter for imaging an anterior ocular segment is attached to an OCT apparatus for imaging a fundus, and when an imaging field angle is changed, a wide angle lens adapter is attached in place of the adapter for imaging an anterior ocular segment. In addition, in this configuration, it is determined whether or not the adapter for imaging an anterior ocular segment is attached, and a result of the determination is displayed on a monitor.

CITATION LIST

Patent Literature

PTL 1: Japanese Patent Application Laid-Open No. 2011-147609

SUMMARY OF INVENTION

Technical Problem

In general, an OCT apparatus used for such a fundus inspection as described above conducts a focus adjustment based on a diopter of an eye to be inspected. The focus adjustment is conducted by moving a focus adjustment mechanism inside the apparatus so that the image becomes brighter by bringing a light used for an inspection into focus on a fundus portion of the eye to be inspected. On the other hand, use of the above-mentioned wide angle lens adapter requires the focus adjustment to be conducted at a position different from a predetermined position, but a focus position may deviate from a focus adjustment range (movable range of the focus lens) of the eye to be inspected depending on a change amount of the focus position. Therefore, the adjustment to an optimal focus position becomes unable to be conducted, or the focus adjustment itself becomes difficult. Further, the OCT apparatus is further demanded to have an optical system exhibiting a narrower field angle in order to acquire the tomographic image within a narrower fundus range with high resolution power, which leads to the same problem.

In view of the above-mentioned problem, one object of the present invention is to enable the focus adjustment with respect to an object to be inspected even when an optical member for changing a field angle is inserted in order to change the field angle of an image acquiring area of the tomographic image, and to acquire a clear tomographic image with a focus on the object to be inspected.

Solution to Problem

In order to solve the above-mentioned problem, according to one embodiment of the present invention, there is provided an optical tomographic imaging apparatus, including:
 a light source;
 an optical splitter configured to split a light emitted from the light source into a measuring light and a reference light;
 a scanning unit configured to scan an object to be inspected with the measuring light;
 an optical system configured to irradiate the object to be inspected with the measuring light through the scanning unit;
 a detector configured to receive an interference light between a return light of the measuring light from the object to be inspected and the reference light; and
 a calculation processing portion configured to process an output signal from the detector, to thereby acquire a tomographic image of the object to be inspected, in which:
 the optical system includes a focus lens configured to focus the measuring light on the object to be inspected; and
 the optical tomographic imaging apparatus further includes a unit configured to compensate, when an optical member for changing a field angle is inserted between the scanning unit and the object to be inspected in order to change the field angle of an image acquiring area of the tomographic image, a change in a focus position of the focus lens in association with the inserting.

Advantageous Effects of Invention

According to the one embodiment of the present invention, the focus adjustment is enabled with respect to the object to be inspected even when the optical member for changing a field angle is inserted in order to change the field angle of an image acquiring area of the tomographic image, and a clear tomographic image with a focus on the object to be inspected may be acquired.

Further features of the present invention will become apparent from the following description of exemplary embodiments with reference to the attached drawings.

BRIEF DESCRIPTION OF DRAWINGS

FIG. 1 is a diagram for schematically illustrating respective configurations included in an optical system of an OCT apparatus according to a first embodiment of the present invention.

FIG. 2 is a diagram for illustrating how an eye to be inspected is scanned with a measuring light in an x direction in the OCT apparatus according to the first embodiment.

FIG. 3 is a diagram for exemplifying an anterior eye image, a two-dimensional fundus image, and a B-scan image that are displayed on a monitor of the OCT apparatus according to the first embodiment.

FIG. 4 is an explanatory diagram for illustrating a difference of an optical path of the measuring light depending on insertion or removal of an adapter lens.

FIG. 5 is an explanatory diagram for illustrating a difference in an optical path length due to an incident angle of the measuring light on a fundus.

FIG. 6 is a diagram for schematically illustrating respective configurations included in an optical system of an OCT apparatus according to a second embodiment of the present invention.

DESCRIPTION OF EMBODIMENTS

Now, embodiments of the present invention are described with reference to the accompanying drawings. Note that, the following embodiments are not intended to limit the present invention according to the scope of claims, and every combination of features described in the embodiments is not necessarily essential to the solution according to the present invention.

First Embodiment (Compensation of Change in In-Focus Position due to Insertion of Adapter Lens by Insertion of Another Lens)

(Schematic Configuration of Apparatus)

A schematic configuration of an optical tomographic imaging apparatus according to a first embodiment of the present invention is described with reference to FIG. 1.

FIG. 1 is a schematic diagram for illustrating a schematic configuration of an optical system of the optical tomographic imaging apparatus according to the first embodiment. As illustrated in FIG. 1, the optical system includes an optical head 900 and a spectroscope 180. The optical head 900 is formed as a measuring optical system for imaging an anterior eye image of an eye 100 to be inspected, a two-dimensional image of a fundus, and a tomographic image of the fundus. The spectroscope 180 forms a Michelson interferometer described later or the like. Further, an adapter lens 105 is removably inserted into the optical system.

(Optical Systems of Optical Head Portion and Spectroscope)

The configurations of the measuring optical system and the spectroscope according to this embodiment are described with reference to FIG. 1.

First, an inside of the optical head 900 is described. In the inside of the optical head 900, a first dichroic minor 102, a second dichroic minor 103, and a third dichroic mirror 104 are arranged as an optical path separating unit. An objective lens 101-1 is provided so as to be opposed to the eye 100 to be inspected, and the first dichroic mirror 102 is arranged on an optical axis of a reflected light from the eye 100 to be inspected. The second dichroic mirror 103 is arranged on an optical axis of a reflected light from the first dichroic mirror 102. In other words, the light is branched off for each waveband so that an optical axis of a transmitted light through the second dichroic mirror 103 becomes a measuring optical path L1 of an OCT optical system and that the optical axis of the reflected light becomes a fundus observation optical path and a fixation lamp optical path L2. Further, the light is branched off for each waveband so that an optical axis of a transmitted light through the first dichroic mirror 102 becomes an anterior ocular segment observation optical path L3. The third dichroic mirror 104 is used to further branch off the fundus observation optical path and the fixation lamp optical path L2 for each waveband as described later.

The fundus observation optical path and the fixation lamp optical path L2 include an X scanner and a Y scanner that form a scanning unit described later, and also include a configuration for obtaining the two-dimensional image of the fundus by scanning the fundus of the eye 100 to be inspected with an illumination light. In this case, it is preferred that the scanning unit be arranged at a position conjugate with an anterior ocular segment of the eye 100 to be inspected, to scan the fundus with a measuring light. At this time, vignetting of the measuring light in the anterior ocular segment can be reduced. Further, the light is branched off into an optical path leading to a light source 114 for observing a fundus and an optical path leading to a fixation lamp 119 for each waveband by the third dichroic minor 104. On the fundus observation optical path and the fixation lamp optical path L2, a lens 101-2, an X scanner 117-1, a Y scanner 117-2, a removable lens 111, an in-focus lens 112, an optical path separation member 118, a lens 113-1, and the third dichroic mirror 104 are arranged in the stated order from the second dichroic mirror 103.

The light source 114 generates a light having a wavelength of 780 nm. The in-focus lens 112 is driven along an optical axis direction (arrow direction in FIG. 1) by a motor (not shown) for the purpose of in-focus adjustment of the fixation lamp 119, a single detector 116 for observing a fundus, and the light source 114. The fixation lamp 119 is used to promote fixation of the eye 100 to be inspected toward an arbitrary direction, and is formed of, for example, a laser or a light emitting diode (LED) configured to emit a light having a wavelength of a visible range. Further, the X scanner 117-1 and the Y scanner 117-2 are each a scanning unit used for scanning the fundus of the eye 100 to be inspected with the illumination light emitted from the light source 114. The lens 101-2 is arranged with a focus position set in a vicinity of a center position of the X scanner 117-1 and the Y scanner 117-2. The X scanner 117-1 is formed of a polygon mirror in order to conduct a high-speed scan in the x direction with the illumination light. In addition, the X scanner 117-1 may be formed of a resonance mirror. Note that, the optical paths between the Y scanner 117-2 and a pinhole 115 described later, the light source 114, and the fixation lamp 119 are formed in the drawing sheet, but are actually formed in the vertical direction with respect to the drawing sheet. When a size increases in the vertical direction with respect to the drawing sheet, a configuration in which each of the optical paths is folded by a mirror (not shown) may be employed.

A lens 113-2, the pinhole 115, and the single detector 116 are arranged on the optical path of the reflected light from the optical path separation member 118. The pinhole 115 is arranged at a position substantially conjugate with the fundus, and a confocal optical system is formed by the fundus and the pinhole 115 arranged at a position conjugate therewith. The illumination light from the light source 114 that has scanned the fundus is scattered and reflected by the fundus. The light that has been scattered or reflected has only a necessary light transmitted through the pinhole 115, to be received by the single detector 116. The single detector 116 is formed of an avalanche photodiode (APD). The optical path separation member 118 is a holed minor or a prism onto which a hollow mirror has been evaporated, and separates the illumination light from the light source 114 and a return light from the fundus.

On the anterior ocular segment observation optical path L3, a lens 141 and a CCD 142 for observing an anterior eye are arranged in the stated order from the first dichroic mirror 102. The CCD 142 has a sensitivity in a vicinity of a wavelength of an illumination light (not shown) for observing an anterior eye, specifically, 970 nm.

The measuring optical path L1 defines the OCT optical system as described above, and is used to image the tomographic image of the fundus of the eye 100 to be inspected. More specifically, the measuring optical path L1 is used to obtain an interference signal for forming the tomographic image.

On the measuring optical path L1, a lens 101-3, a mirror 121, an OCT X scanner 122-1, an OCT Y scanner 122-2, an OCT in-focus lens 123, an OCT removable lens 127, a lens 124, and a fiber end 126 are arranged in the stated order from the second dichroic mirror 103. Those components form a part of the optical system configured to irradiate an eye to be inspected with the measuring light for OCT described later. The OCT X scanner 122-1 and the OCT Y scanner 122-2 each provided as a scanning unit for the measuring light are arranged in order to scan the fundus of the eye 100 to be inspected with the measuring light.

The fiber end 126 makes the measuring light incident on a measuring optical path, and is used as a light source for the measuring light in this embodiment. In this embodiment, the fiber end 126 has an optically conjugate relationship with a fundus portion of the eye 100 to be inspected. The OCT in-focus lens 123 is driven along the optical axis direction (arrow direction in FIG. 1) by a motor (not shown) for the purpose of the in-focus adjustment of the measuring light with respect to the fundus. The OCT in-focus lens 123 forms a focus lens configured to focus the measuring light on the eye 100 to be inspected. The in-focus adjustment is conducted so that a light emitted from the fiber end 126 that functions as a measuring light source is imaged on the fundus. Note that, the optical path between the OCT X scanner 122-1 and the OCT Y scanner 122-2 is formed in the drawing sheet, but is actually formed in the vertical direction with respect to the drawing sheet.

Next, configurations of an optical path extending from a light source 130 to the fiber end 126, a reference optical system, and the spectroscope are described. The light emitted from the light source 130 passes through an optical fiber 125-1, and reaches an optical coupler 125. The optical fiber 125-1 and optical fibers 125-2, 125-3, and 125-4 in a single mode are connected to the optical coupler 125. The light that has reached the optical coupler 125 is split into the measuring light and a reference light at the optical coupler 125. The measuring light is guided to the measuring optical path L1 through the optical fiber 125-2, and the reference light is guided to the reference optical system through the optical fiber 125-3. The optical coupler 125 forms an optical splitter configured to split the light emitted from the light source 130 into the measuring light and the reference light. An emitting end portion of the optical fiber 125-2 corresponds to the fiber end 126. The measuring light passes through the optical path for the OCT optical system described above, and is applied to the fundus of the eye 100 to be inspected, which is an observation target. Then, the measuring light is caused to pass through the same optical path by being reflected or scattered by a retina, to thereby reach the optical coupler 125.

In the reference optical system, a lens 151, removable dispersion compensation glass 154, a dispersion compensation glass 152, and a mirror 153 are arranged in the stated order from the emitting end portion of the optical fiber 125-3. Those components form a Michelson interferometer together with the spectroscope 180 described later. The spectroscope 180 forms a detector configured to receive an interference light between the return light from the eye 100 to be inspected and the reference light.

The reference light emitted from the emitting end portion of the optical fiber 125-3 passes through the lens 151 and the dispersion compensation glass 152, reaches the mirror 153, and is reflected by the mirror 153. The dispersion compensation glass 152 is inserted in the optical path in order to match dispersion of the measuring light and dispersion of the reference light with each other. The reference light reflected by the mirror 153 follows back the same optical path to reach the optical coupler 125. The removable dispersion compensation glass 154 is dispersion compensation glass that can be inserted into the optical path or removed from within the optical path. When the adapter lens 105 described later is not inserted yet, the removable dispersion compensation glass 154 is removed from within the optical path, and in contrast, when the adapter lens 105 is inserted, the removable dispersion compensation glass 154 is inserted into the optical path.

The measuring light being the return light returned from the eye 100 to be inspected and the reference light reflected by the mirror 153 are multiplexed by the optical coupler 125, and becomes the interference light. In this case, interference occurs when an optical path length of the return light and an optical path length of the reference light become substantially the same. The mirror 153 is held so as to be adjustable in the optical axis direction by a motor (not shown) and a drive mechanism (not shown) driven by a mirror control system 173. This enables the mirror 153 to match the optical path length of the reference light with the optical path length of the return light, which is changed depending on the eye 100 to be inspected. The interference light is guided to the spectroscope 180 through the optical fiber 125-4.

The spectrometer 180 includes lenses 181 and 183, a diffraction grating 182, and a line sensor 184. The interference light emitted from the optical fiber 125-4 is substantially collimated through the lens 181 and dispersed by the diffraction grating 182 to form an image on the line sensor 184 by the lens 183. Information on a luminance distribution of the interference signal acquired by the line sensor 184 provided as a detector is output to a calculation processing portion 174 as an output signal, and is constructed and acquired as the tomographic image in the calculation processing portion 174. In other words, the calculation processing portion 174 forms a calculation processing portion configured to process the output signal from the spectroscope 180, to thereby acquire the tomographic image of the fundus of the eye 100 to be inspected.

Next, the periphery of the light source 130 is described. The light source 130 is a super luminescent diode (SLD), which is a typical low coherent light source. A light emitted from the light source 130 has a central wavelength of 855 nm and a wavelength band width of about 100 nm. In this case, the band width influences a resolution in an optical axis direction of a tomographic image to be acquired, and hence, is an important parameter. Further, although the SLD is selected, the type of the light source is not particularly limited as long as the light source is capable of emitting a low coherent light. Considering the measurement of an eye, a near-infrared light is suitable for the central wavelength.

Further, it is desired that the central wavelength be a shortest possible wavelength because the central wavelength influences a resolution in a lateral direction of a tomographic image to be acquired. For both the reasons, the central wavelength of this embodiment is set to 855 nm.

Note that, although the Michelson interferometer is used as an interferometer in this embodiment, a Mach-Zehnder interferometer may be used. It is desired that the Mach-Zehnder interferometer be used in the case where an optical amount difference between the measuring light and the reference light is large, and the Michelson interferometer be used in the case where the optical amount difference is relatively small.

Operations of scanners and the like within the optical head 900 described above, lighting control of the fixation lamp 119, imaging of an image, construction of the image based on intensity information acquired from the OCT optical system, and other such operations are controlled and executed by a control portion 170. Further, insertion or removal of the removable lens 111, the OCT removable lens 127, the removable dispersion compensation glass 154, and the adapter lens 105 described later into or from the optical path is controlled by an insert/remove control system 171 through a drive mechanism (not shown). The control is described later in detail. The movement of the in-focus lens 112 and the OCT in-focus lens 123 along the optical axis for attaining an in-focus state, control of the moving range, and the like are executed by a drive control system 172. Further, the movement of a center position of the mirror 153 is executed by the minor control system 173.

(Adapter Lens)

In this embodiment, the adapter lens 105 to be removably inserted is assumed to be inserted between the objective lens 101-1 and the eye 100 to be inspected at a time of wide angle imaging. The adapter lens 105 forms an optical member for changing a field angle to be inserted between the OCT X scanner 122-1 provided as a scanning unit and the eye 100 to be inspected in order to change a field angle of an image acquiring area of the tomographic image. In other words, the adapter lens 105 is assumed to be inserted in a vicinity of the eye 100 to be inspected in this embodiment due to easy configuration thereof or other such factors, but a mode of inserting the adapter lens 105 in the above-mentioned position on the measuring optical path L1 may be employed. Further, a mode in which the adapter lens 105 is inserted into the optical path by a manual operation or the like, the insertion is detected by the control portion 170, and control corresponding to each control system is executed may be employed. Further, a unit configured to conduct the operation for the insertion may be provided so as to execute the widening of the field angle in response to an instruction therefor received by the control portion 170. The insertion of the adapter lens 105 allows observation of a wide region of the fundus portion of the eye 100 to be inspected.

Note that, it is desired that the adapter lens 105 be a convex lens for a reason described later. Further, in order to change an angle of a light converged on a pupil position of the eye 100 to be inspected, it is desired that the adapter lens 105 be a meniscus lens when convergence on the pupil is taken into consideration. Further, the adapter lens 105 may be provided to the apparatus, or may be an eyeglass-type object to be attached to a subject. It is desired that the eyeglass-type object be a lens for correcting a plus diopter for the above-mentioned reason.

The focus position of the optical system is changed due to the insertion or removal of the adapter lens 105, and hence the measuring optical path L1 of the OCT optical system includes the OCT removable lens 127 so as to correct the focus position. When the adapter lens 105 is not inserted yet, the OCT removable lens 127 is removed from within the optical path, and in contrast, when the adapter lens 105 is inserted, the OCT removable lens 127 is inserted into the optical path. The insertion or removal of the OCT removable lens 127 into or from the optical path depending on the insertion or removal of the adapter lens 105 is controlled by the insert/remove control system 171.

In the same manner, the removable lens 111 is also removably inserted into the fundus observation optical path and the fixation lamp optical path L2. When the adapter lens 105 is not inserted yet, the removable lens 111 is removed from within the optical path, and in contrast, when the adapter lens 105 is inserted, the removable lens 111 is inserted into the optical path. The insertion or removal of the removable lens 111 into or from the optical path depending on the insertion or removal of the adapter lens 105 is also controlled by the insert/remove control system 171 in the same manner. Further, the in-focus adjustment using the OCT in-focus lens 123 and the in-focus lens 112 is conducted by changing each position depending on the diopter of the eye to be inspected. The movement of those in-focus lenses along the optical axis depending on the diopter is controlled by the drive control system 172.

However, a magnification relationship between the measuring light source 126 and the fundus of the eye 100 to be inspected, a magnification relationship between the fixation lamp 119 and the fundus of the eye 100 to be inspected, a magnification relationship between the pinhole 115 and the eye 100 to be inspected, and a magnification relationship between the light source 114 and the eye 100 to be inspected are changed depending on the insertion or removal of the OCT removable lens 127 and the removable lens 111 into or from the optical path. Therefore, in this embodiment, when the movement of the OCT in-focus lens 123 and the in-focus lens 112 on the optical path is controlled by the drive control system 172, a moving amount thereof is changed.

Note that, for example, the drive control system 172 configured to control the movement of those in-focus lenses may include two tables relating to the moving amount for each case of presence or absence of a removable lens on the optical path. In this case, the table may be selected for each case, or the position to attain the in-focus state may be freely selected by an inspector.

Now, when the dispersion compensation glass 152 and the removable dispersion compensation glass 154 are arranged in the reference optical system, consideration is required to be given to a group speed GD exhibited when the reference light is transmitted through the glass. The group speed GD is expressed by the following expression.

$$GD = dng/d\lambda = -\lambda \times d^2n/d\lambda^2 \qquad 1$$

In the expression, $ng = n - \lambda \times dn/d\lambda$, $\lambda$ represents a central wavelength of the light source 130, $dng/d\lambda$ represents a wavelength differential of a group refractive index $ng$, $d^2n/d\lambda^2$ represents a second-order differential of a wavelength of a refractive index $n$, and $dn/d\lambda$ represents a wavelength differential of a refractive index.

In other words, dispersion compensation for the measuring optical path and a reference optical path is conducted by obtaining the group speed GD of optical elements and configuring the optical elements so that a product (GD×L) of the group speed GD and a thickness L of the optical elements in the optical axis direction has the same value for the measuring optical path and the reference optical path. In this embodiment, when the adapter lens 105 and the OCT removable lens 127 are inserted into the measuring optical path L1, glass corresponding to a total of GD×L of the adapter lens 105 and the OCT removable lens 127 is inserted into the reference optical path as a dispersion compensation unit. In this embodiment, the dispersion compensation unit is formed by the removable dispersion compensation glass 154. The insertion of the dispersion compensation unit into the optical path of the reference light allows cancellation of the dispersion of the light that occurs in the optical system due to the insertion of the adapter lens 105, and allows the acquisition of a clear tomographic image exhibiting no blur.

Note that, a method of correcting a group speed through use of the optical elements inside the apparatus is described above, but on the other hand, the dispersion compensation may also be conducted by a calculation parameter. The dispersion compensation may be conducted not by inserting or removing the removable dispersion compensation glass 154 but by changing a calculation parameter value. Calculation for the dispersion compensation is conducted by the following expression.

$$d(k) = \beta k^2 \quad \quad 2$$

In the expression, k represents a wave number, and is expressed by $k = 1/\lambda$. $\beta$ represents a parameter of the dispersion compensation, and the changing of the parameter $\beta$ allows the correction of the difference in the dispersion between the measuring optical path and the reference optical path. In other words, the change in the dispersion due to the insertion or removal of the adapter lens 105 and the OCT removable lens 127 can also be corrected by using the parameter $\beta$. In that case, the removable dispersion compensation glass 154 is not required. In other words, in this mode, the changing of the parameter $\beta$ of the dispersion compensation serving as a correction parameter of the output signal from the spectroscope 180 reduces influence of the dispersion of the light that occurs due to the insertion of the adapter lens 105 into the optical system. The correction is conducted by the calculation processing portion 174, and the calculation processing portion 174 forms a unit configured to correct an output signal from the detector.

Further, the insertion of the adapter lens 105 causes a change in a distance between the optical head 900 and the eye 100 to be inspected, and hence optical path lengths of the measuring optical path and the reference optical path are changed. Therefore, this embodiment includes a mechanism for causing the mirror control system 173 to change the center position of the mirror 153 in the optical axis direction depending on the insertion or removal of the adapter lens 105.

As described above, in an OCT apparatus, it is preferred that a relationship between the optical path length and wavelength dispersion of the optical member be substantially matched between the measuring optical path and the reference optical path. However, the relationship fails to be maintained when a wide angle lens adapter is used, which may inhibit the tomographic image from being displayed satisfactorily or may obtain a blurred image. As in this embodiment, the insertion or removal of the removable dispersion compensation glass 154 configured to compensate the dispersion is executed depending on the insertion or removal of the adapter lens 105, to thereby obtain the clear tomographic image exhibiting no blur.

(Imaging Method for Tomographic Image)

An imaging method for the tomographic image using the optical tomographic imaging apparatus according to this embodiment is described. The optical tomographic imaging apparatus controls the OCT X scanner 122-1 and the OCT Y scanner 122-2, to thereby enable the imaging of the tomographic image at a desired site on the fundus of the eye 100 to be inspected.

FIG. 2 is an illustration of how the eye 100 to be inspected is irradiated with a measuring light 201, and a fundus 202 is scanned in the x direction. Information on a predetermined number of imaging lines is imaged by the line sensor 184 from an imaging range in the x direction on the fundus 202. A signal of the luminance distribution on the line sensor 184 obtained at a given position in the x direction is subjected to a wave number conversion, the calculation for the dispersion compensation, and a Fourier transform (FFT) by the calculation processing portion 174. The information converted into a density or color information in order to indicate a linear luminance distribution obtained by the FFT on a monitor is referred to as "A-scan image". A two-dimensional image obtained by arraying a plurality of A-scan images described above is referred to as "B-scan image". A plurality of A-scan images used for constructing one B-scan image are imaged, and then the scan in the x direction is again conducted while a scanning position in the y direction is moved, to thereby obtain a plurality of B-scan images. The B-scan image is further subjected to processing such as luminance adjustment by the calculation processing portion 174, and is displayed on a screen.

The plurality of B-scan images or a three-dimensional tomographic image constructed of the plurality of B-scan images is displayed on the monitor, to thereby be usable by the inspector for a diagnosis of the eye to be inspected.

In FIG. 3, an anterior eye image 210, a two-dimensional fundus image 211, and a B-scan image 212 being the tomographic image, which are displayed on a monitor 200 connected to the control portion 170, are illustrated. The anterior eye image 210 is an image displayed after being processed by the calculation processing portion 174 based on an output from the CCD 142. The two-dimensional fundus image 211 is an image displayed after being processed by the calculation processing portion 174 based on an output from the single detector 116. Further, the B-scan image 212 is an image displayed after being constructed through the above-mentioned processing based on an output from the line sensor 184.

FIG. 4 is a diagram for illustrating an optical path exhibited when the adapter lens 105 is not inserted yet and a diagram for illustrating an optical path exhibited when the adapter lens 105 is inserted in the optical path, which are arranged vertically for comparison. In comparison between the two diagrams, it is understood that the insertion or removal of the adapter lens 105 allows a scanning range of the fundus 202 to be changed. In other words, the insertion of the adapter lens 105 allows the scanning range of the fundus 202 to become wider than when the adapter lens 105 is not inserted yet.

Now, assuming that a focus distance of the objective lens 101-1 is f1, a focus distance of the adapter lens 105 is f2, and a distance between principal points of the two lenses is e, a synthetic focus distance F between the lens 101-1 and the adapter lens 105 is expressed by the following expression.

$$1/F = 1/f1 + 1/f2 - e \times 1/f1 \times 1/f2 \quad \quad 3$$

For example, F=22.5 mm is established when assuming that the distance between the principal points of convex lenses having f1=45 mm and f2=30 mm is 15 mm. This allows an angular magnification with respect to the OCT X scanner 122-1 and the OCT Y scanner 122-2 to become larger than when only the objective lens 101-1 is used. This allows the eye 100 to be inspected to be scanned with a wider field angle θ, to thereby acquire the image.

In FIG. 4, a fundus-conjugate position 203 on the optical axis is illustrated. The adapter lens 105 is formed of a convex lens, and hence the fundus-conjugate position 203 becomes closer to the objective lens 101-1 when the adapter lens 105 is inserted. Therefore, the focus position is corrected by the OCT removable lens 127 so as to correspond to the fundus-conjugate position 203. In this embodiment, the correction is conducted in a direction in which the focus position becomes farther from the OCT removable lens 127, and hence the OCT removable lens 127 is formed of a concave lens.

Next, when attention is paid to a position of the eye 100 to be inspected, it is understood that the position (working distance) is required to be changed by inserting or removing the adapter lens 105. In this case, the working distance corresponds to the distance between the eye 100 to be inspected and the optical head 900 exhibited when a preferred image is obtained. Alignment of the optical head 900 and the eye 100 to be inspected is conducted so as to attain the above-mentioned working distance. The working distance becomes shorter by the insertion of the adapter lens 105, and hence the optical tomographic imaging apparatus includes a mechanism for causing the mirror control system 173 to change the center position of the mirror 153 on the optical axis within the reference optical path depending on the insertion or removal of the adapter lens 105.

Further, when the scanning is conducted with a wide field angle by the insertion of the adapter lens, there also occurs a problem of a distortion increased at positions near both end portions of the tomographic image.

In FIG. 5, a factor of a difference in the optical path length ascribable to a difference in an incident angle on the fundus of the eye 100 to be inspected is illustrated. The incident angle is approximately a right angle with respect to a retinal layer in a vicinity of a center, but in a periphery of the imaged tomographic image, the incident angle deviates from the right angle, which necessitates the correction of the retina thickness. This tendency becomes more conspicuous through the scanning with a wider field angle. Assuming that an actual retina thickness is t, an optical path length of a light beam within the retina along an incident direction is d, and the incident angle on the fundus is α, the following expression is established.

$$t = d \times \cos(\alpha) \quad \quad 4$$

The optical path length d is a value obtained from the tomographic image in actuality.

The incident angle α cannot be actually measured because of being an incident angle inside the actual eye to be inspected, and is therefore calculated by the following method. In this case, the parameters (refractive index, curvature, and thickness) of the optical system of the apparatus and the parameters (refractive index, curvature, and thickness) of the adapter lens 105 are grasped in advance. In addition, optical characteristics such as shape data on a cornea, a crystalline lens, and the like of the eye 100 to be inspected, which are measured in advance, are used to track the light beam, to thereby enable the incident angle α to be calculated. Further, it is preferred that a relationship between swing angles of the OCT X scanner 122-1 and the OCT Y scanner 122-2 and the incident angle α is obtained in advance also regarding the parameters of the optical system of the apparatus and the parameters of the adapter lens. In this case, those values may be actually measured by using a model eye as a reference, and may be stored in a memory (not shown) or the like included in the control portion 170. After that, the shape data on the cornea, the crystalline lens, and the like of the eye 100 to be inspected, which are measured in advance, may be used to calculate the incident angle α. Note that, the above-mentioned operations are executed by a module within the calculation processing portion 174 that functions as a correction unit configured to correct a distortion of the tomographic image based on the optical characteristic of the adapter lens 105 and the optical characteristic of the cornea of the eye 100 to be inspected.

In general, when the image is acquired with a wide field angle, there is a problem of a distortion increased at the positions near the both end portions of the image. However, when the calculation of such an incident angle α, the calculation of the retina thickness based thereon, and the image correction are conducted, the image without a distortion in an overall image display region is obtained.

Second Embodiment (Movement of Center Position of Drive Region for In-Focus Lens)

Next, an optical tomographic imaging apparatus (OCT apparatus) according to a second embodiment of the present invention is described with reference to FIG. 6.

(Schematic Configuration of Apparatus)

A schematic configuration of the optical tomographic imaging apparatus according to this embodiment is substantially the same as that described in the first embodiment, and hence the same components are denoted by the same reference symbols, and descriptions thereof are omitted below.

(Optical Systems of Optical Head Portion and Spectroscope)

A difference from the first embodiment is described. The first embodiment is described by taking an example in which the change in the focus position of the optical system due to the insertion or removal of the adapter lens 105 is corrected by inserting or removing the OCT removable lens 127 and the removable lens 111. In the second embodiment, an operation of matching the focus position with the fundus-conjugate position 203 illustrated in FIG. 4 is conducted by shifting a center position or the like of drive regions for the OCT in-focus lens 123 and the in-focus lens 112.

In this embodiment, the in-focus lens 112 and the OCT in-focus lens 123 include a drive center changing mechanism (not shown) for moving the center position of the drive region. Note that, the drive center changing mechanism is controlled by the drive control system 172, and may be constructed as a structural or controllable configuration. Those configurations are used to offset the position of a movable center of a movable range for the in-focus lens, and as described above, it is preferred that an offset amount therefor be calculated and set based on a diopter of the adapter lens 105. Further, the movable range may be maintained, or may be extended or shortened based on the diopter or the like.

In other words, when the adapter lens 105 is not inserted yet, the in-focus lens 112 and the OCT in-focus lens 123 are arranged at original center positions, and each correct a predetermined diopter of the eye to be inspected while being moved within a drive range having the center position set as a reference. On the other hand, when the adapter lens 105 is inserted, the in-focus lens 112 and the OCT in-focus lens 123 have their center positions moved, and each correct the predetermined diopter of the eye to be inspected while being moved within a drive range having the moved center position set as a center. This is because the insertion of the adapter lens 105 causes a movement of the fundus-conjugate position 203 illustrated in FIG. 4, and the in-focus lens 112 and the OCT in-focus lens 123 are caused to move in accordance with the movement of the fundus-conjugate position. Magnifications of the measuring light source 126 and the eye 100 to be inspected are changed in the same manner as in the first embodiment, and hence the moving amount is also changed in the same manner. Note that, it is preferred that the moving amount or the drive range be also restricted by the drive control system 172.

In addition, glass corresponding to GD×L of the adapter lens 105 is inserted into the reference optical path as the removable dispersion compensation glass 154. This allows the clear tomographic image exhibiting no blur to be obtained.

Other Embodiments

In the first embodiment, the change in the focus position of the optical system due to the insertion or removal of the adapter lens 105 is corrected by inserting or removing the OCT removable lens 127 and the removable lens 111 into or from the optical path. Further, in the second embodiment, the correction is conducted by shifting the center positions of the drive ranges for the OCT in-focus lens 123 and the in-focus lens 112. However, the present invention is not particularly limited to the forms described in those embodiments, and may be carried out by combining those two forms. More specifically, the correction may be conducted by inserting or removing the OCT removable lens 127 and the removable lens 111 into or from the optical path and shifting the center positions of the drive ranges for the OCT in-focus lens 123 and the in-focus lens 112. In an embodiment of the combined forms, the dispersion compensation is required to be conducted for the adapter lens 105 and the OCT removable lens 127, and hence the removable dispersion compensation glass 154 corresponding thereto is removably inserted into the reference optical system. A characteristic of the removable dispersion compensation glass 154 is determined in the same manner as in the first embodiment.

This embodiment is particularly useful when the adapter lens 105 is an eyeglass-type optical member. In the case of such an eyeglass-type lens, there is a problem in that a focus distance or a diopter value of the lens to be attached to the subject is unknown. Accordingly, in this case, a position where a focus is achieved is required to be found. In search for the position where a focus is achieved, a large change in the focus position is corrected roughly by inserting the OCT removable lens 127 and the removable lens 111 into the optical path. In a detailed search for the focus position conducted subsequently, the adjustment is enabled through a shift in in-focus positions of the OCT in-focus lens 123 and the in-focus lens 112. The adjustment through the shift may be manually conducted by the inspector so that the tomographic image and a two-dimensional fundus image become brighter, or may be automatically conducted by the apparatus.

Note that, the present invention may be applied to the case of using eyeglasses in place of the adapter lens 105, and the configuration that can support the adapter lens 105 is not limited thereto. A contact lens or any other optical member that can be inserted into the measuring optical path in order to change the field angle may be employed as an insert lens therefor as long as the optical member is removably inserted between the scanning unit within the OCT apparatus and the eye to be inspected and enables the changing of the field angle. Further, the present invention may be applied not only to the insertion of the optical member used for achieving a wider field angle, but also to the insertion of an optical member used for achieving a narrower field angle.

Further, both the first embodiment and the second embodiment are described by taking an exemplary case of a spectral domain OCT (SD-OCT) configured to detect the light source having a spectrum width through use of the spectroscope, but the present invention is not limited thereto. The present invention may be applied to a time domain OCT (TD-OCT) including a spectroscope portion formed of a single detector, and to a swept source OCT (SS-OCT) formed of a detector for differential detection with a wavelength sweeping light source used as a light source. In other words, those apparatus are also enabled to produce the same effects by including the measuring optical path and the reference optical path configured as those in the first embodiment or in the second embodiment. However, the reference optical path for the SS-OCT configured to conduct the differential detection is required to be formed of an incident light and an emitted light that have different paths. Therefore, the removable dispersion compensation glass 154 is required to be inserted with a thickness determined with the above-mentioned point taken into consideration.

As described above, the focus position based on the OCT in-focus lens 123 and the like is changed depending on the insertion of the adapter lens 105 into the optical path. In the above-mentioned embodiments, the removable lens is inserted into the optical system as the optical member configured to cancel the change in the focus position, or the offset is conducted depending on the change in the focus position of the movable center of the movable range for the focus lens, to thereby handle the change in the focus position. Accordingly, those configurations produce an effect of compensating the change in the focus position in association with the insertion of the adapter lens 105 into the optical path, and it is preferred that those configurations be grasped as a unit configured to compensate the change as well as another mode enabled to produce the same effect.

Note that, the present invention is not limited to the above-mentioned embodiments, and may be conducted with various changes and modifications within the scope that does not depart from the gist of the present invention. For example, the description of the above-mentioned embodiments is directed to the case where an object to be inspected is an eye, but the present invention may be applied to an object to be inspected such as a skin or an organ other than the eye. In this case, the present invention has a mode as medical equipment such as an endoscope other than the ophthalmic apparatus. Accordingly, it is desired that the present invention be grasped as an optical tomographic imaging apparatus exemplified by the ophthalmic apparatus, and the eye to be inspected be grasped as one mode of the object to be inspected.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD) (Trade Mark)), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-003427, filed Jan. 9, 2015, which is hereby incorporated by reference herein in its entirety.

The invention claimed is:

1. An optical tomographic imaging apparatus, comprising:
   a light source;
   an optical splitter configured to split a light emitted from the light source into a measuring light and a reference light;
   a scanning unit configured to scan a fundus of an eye to be inspected with the measuring light;
   an optical system configured to irradiate the fundus with the measuring light through the scanning unit;
   a detector configured to receive an interference light between (1) a return light of the measuring light from the fundus and (2) the reference light; and
   a calculation processing portion configured to process an output signal from the detector, to thereby acquire a tomographic image of the fundus,
   wherein the optical system comprises a focus lens configured to focus the measuring light on the fundus, and
   wherein the optical tomographic imaging apparatus further comprises a unit configured to compensate, when an optical member for changing a field angle is inserted between the scanning unit and the fundus in order to change the field angle of an acquiring area of the tomographic image of the fundus, a change in a focus position of the focus lens with respect to the fundus, in association with the inserting.

2. An optical tomographic imaging apparatus according to claim 1, wherein the unit configured to compensate the change comprises a unit configured to offset a movable center of a movable range for the focus lens so as to correspond to the change in the focus position.

3. An optical tomographic imaging apparatus according to claim 2, wherein the unit configured to offset the movable center is further configured to set an offset amount based on a diopter of the inserted optical member for changing a field angle.

4. An optical tomographic imaging apparatus according to claim 1, wherein the unit configured to compensate the change comprises a removable optical member to be inserted into the optical system in order to cancel the change in the focus position.

5. An optical tomographic imaging apparatus according to claim 1, further comprising a dispersion compensation unit to be inserted into an optical path of the reference light in order to cancel dispersion of a light that occurs in the optical system due to insertion of the optical member for changing a field angle.

6. An optical tomographic imaging apparatus according to claim 1, further comprising a unit configured to correct the output signal from the detector so as to reduce influence of dispersion of a light that occurs in the optical system due to insertion of the optical member for changing a field angle.

7. An optical tomographic imaging apparatus according to claim 1, wherein the optical member for changing a field angle comprises an eyeglass-type optical member to be attached to a subject.

8. An optical tomographic imaging apparatus according to claim 7, wherein the unit configured to compensate the change is further configured to calculate, when offsetting a movable center of a movable range for the focus lens so as to correspond to the change in the focus position, an offset amount for the offsetting based on the attached eyeglass-type optical member, and offset the movable center of the movable range for the focus lens by the calculated offset amount.

9. An optical tomographic imaging apparatus according to claim 1, further comprising a unit configured to insert and remove the optical member for changing a field angle into and from the optical system.

10. An optical tomographic imaging apparatus according to claim 1, wherein the optical member for changing a field angle comprises any one of a convex lens, a meniscus lens, an eyeglass-type lens, and a contact-type lens.

11. An optical tomographic imaging apparatus according to claim 1, wherein the optical tomographic imaging apparatus further comprises a correction unit configured to correct a distortion of the tomographic image based on an optical characteristic of the optical member for changing a field angle and an optical characteristic of a cornea of the eye to be inspected.

12. An optical tomographic imaging apparatus according to claim 1, wherein the scanning unit is arranged at a position conjugate with an anterior ocular segment of the eye to be inspected, and is further configured to scan the fundus with the measuring light.

13. A method of controlling an optical tomographic imaging apparatus, the optical tomographic imaging apparatus comprising: (a) a light source; (b) an optical splitter configured to split a light emitted from the light source into a measuring light and a reference light; (c) a scanning unit configured to scan a fundus of an eye to be inspected with the measuring light; (d) an optical system configured to irradiate the fundus with the measuring light through the scanning unit; (e) a detector configured to receive an interference light between (1) a return light of the measuring light from the fundus and (2) the reference light; and (f) a calculation processing portion configured to process an output signal from the detector, to thereby acquire a tomographic image of the fundus, wherein the optical system comprises a focus lens configured to focus the measuring light on the fundus, the method comprising:
   compensating, when an optical member for changing a field angle is inserted between the scanning unit and the fundus in order to change the field angle of an acquiring area of the tomographic image of the fundus, a change in a focus position of the focus lens with respect to the fundus, in association with the inserting.

14. A non-transitory tangible medium having recorded thereon a program for causing a computer to execute the control method for an optical tomographic imaging apparatus of claim 13.

* * * * *